United States Patent
Kuroda et al.

Patent Number: 5,134,049
Date of Patent: Jul. 28, 1992

[54] PHOTOCONDUCTOR FOR ELECTROPHOTOGRAPHY

[75] Inventors: Masami Kuroda; Masayo Amano; Noboru Furusho, all of Kanagawa, Japan

[73] Assignee: Fuji Electric Co., Ltd., Kanagawa, Japan

[21] Appl. No.: 757,294

[22] Filed: Sep. 10, 1991

[30] Foreign Application Priority Data

Sep. 11, 1990 [JP] Japan .................. 1-240228

[51] Int. Cl.$^5$ .................. G03G 5/09; G03G 5/047
[52] U.S. Cl. .................. 430/58; 430/56; 430/83
[58] Field of Search .................. 430/56, 58, 83

[56] References Cited

U.S. PATENT DOCUMENTS

| | | | |
|---|---|---|---|
| 3,189,447 | 6/1965 | Neugebauer et al. | 430/77 |
| 4,956,250 | 9/1990 | Kuroda et al. | 430/58 |

FOREIGN PATENT DOCUMENTS

| | | | |
|---|---|---|---|
| 120258 | 7/1983 | Japan | 430/58 |
| 19147 | 1/1985 | Japan | 430/58 |
| 30853 | 2/1988 | Japan | 430/58 |

Primary Examiner—Roland Martin
Attorney, Agent, or Firm—Spencer, Frank & Schneider

[57] ABSTRACT

A photoconductor for electrophotography comprises an electroconductive substrate and a photosensitive layer formed thereon and including a novel compound as a charge transporting substance. This compound is represented by the following general formula:

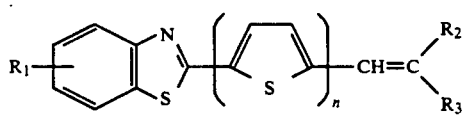

wherein, R1 is selected from the group consisting of a hydrogen atom, a halogen atom, an alkyl group and an alkoxy group, each of R2 and R3 is selected from the group consisting of an alkyl group, an aryl group and a heterocyclic group, the last two groups of which may be substituted and n is an integer of 1 or 2.

8 Claims, 1 Drawing Sheet

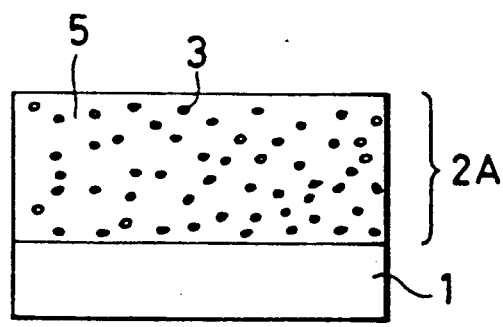
F I G. 1
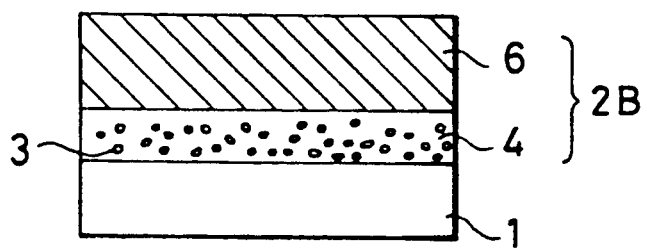
F I G. 2
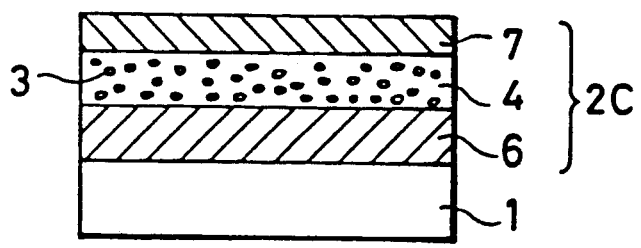
F I G. 3

PHOTOCONDUCTOR FOR ELECTROPHOTOGRAPHY

BACKGROUND OF THE INVENTION

1. Field of the Invention

The present invention relates to a photoconductor for electrophotography, and more particularly to a photoconductor for electrophotography which contains a novel compound as a charge transporting substance in the photosensitive layer of on an electroconductive substrate.

2. Description of the Prior Art

Photosensitive materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and bisazo compounds, and dispersions of such organic polymeric photoconductive substances in resin binders.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the transportation of electric charge upon receiving light.

In an electrophotographic method using a photoconductor of the kind as mentioned above, for example, the Carlson system is applied to image formation. The image formation according to this system comprises steps of subjecting a photoconductor in the dark to corona discharge to charge the photoconductor, illuminating the surface of the charged photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralization of the residual charge with light (erasion), and so on to be ready for reuse.

Photoconductors for electrophotography in which use are made of photosensitive organic compounds have recently been put into practical use by virtue of the advantageous features such as flexibility, thermal stability and/or film forming capacity. For example, a variety of charge transporting substances are known as a oxadiazole compound (disclosed in U.S. Pat. No. 3,189,447), as a pyrazoline compound (disclosed in Japanese Patent Application Publication No. 2,023/1984), as a hydrazone compound (disclosed in Japanese Patent Application Publication No. 42,380/1980 or Japanese Patent Application Laying-open No. 101,844/1982), as a triarylamine (disclosed in Japanese Patent Application Laying-open No. 32,327/1983) and as a stilbene compound (disclosed in Japanese Patent Application Laying-open No. 198,043/1983).

Although organic materials have a number of advantageous features mentioned above with which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography to be used in copying apparatuses and printers which photoconductor has a high photosensitivity and excellent characteristics in repeated use, through the use, in the photosensitive layer, of a novel organic materials not used to date as a charge transporting substance.

In the first aspect of the present invention, a photoconductor for electrophotography comprises:

an electroconductive substrate; and a photosensitive layer formed on the electroconductive substrate including a charge generating substance and at least one of the compounds represented by the following general formula (I) as a charge transporting substance:

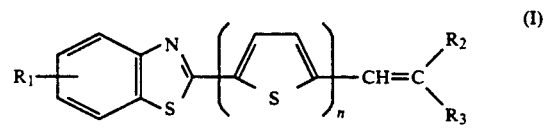

(I)

Wherein R1 is selected form the group consisting of a hydrogen atom, a halogen atom, an alkyl group and an alkoxy group, each of R2 and R3 is selected from the group consisting of an alkyl group, aryl group and a heterocyclic group, the last two groups of which may be substituted and n is an integer of 1 or 2.

Here, the photosensitive layer may be a monolayer containing a charge generating substance and a charge transporting substance.

The photosensitive layer may be composed of a charge generating layer containing a charge generating substance and a charge transporting layer containing the charge transporting substance and laminated on the charge generating layer.

The photosensitive layer may be composed of a charge transporting layer containing the charge transporting substance and a charge generating layer containing a charge generating substance and laminated on the charge transporting layer.

In the second aspect of the present invention, a photoconductor for electrophotography comprises:

an electroconductive substrate, and a photosensitive substrate formed on the electroconductive substrate including a charge generating substance and at least one of the compounds represented by the following general formula (II) as a charge transporting substance:

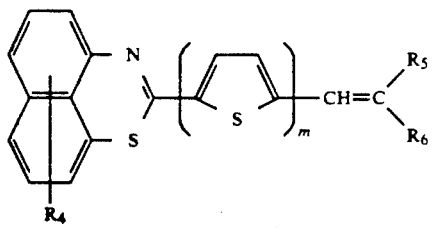

(II)

Wherein, R4 is selected from the group consisting of a hydrogen atom, a halogen atom, an alkyl group and an alkoxy group, each of R5 and R6 is selected from the group consisting of an alkyl group, an aryl group and a heterocyclic group, the last two groups of which may be substituted and m is an integer of 1 or 2.

Here, the photosensitive layer may be a monolayer containing a charge generating substance and the charge transporting substance.

The photosensitive layer may be composed of a charge generating layer containing a charge generating substance and a charge transporting layer containing the charge transporting substance and laminated on the charge generating layer.

The photosensitive layer may be composed of a charge transporting layer containing the charge transporting substance and a charge generating layer containing a charge generating substance and laminated on the charge transporting layer.

The compounds represented by the general formula (I) or (2) are first provided as a charge transporting substance having excellent characteristics in the present invention.

As for the use of the compounds represented by the general formula (I) or (II) give above in the photosensitive layers, there has been no precedent before, The present inventors have been keenly investigated a variety of organic materials in order to solve the above-mentioned problems, and have conducted a number of experiments for these materials and, as a result, have found that the use of specific compounds represented by the above general formula (I) or (II) as a charge transporting substance is very effective in improving electrophotographic characteristics, although the fact has not been given a satisfactory technical explanation as yet. On the basis of this finding, they obtained photoconductors for electrophotography having high sensitivity and good repeated use characteristics.

The above and other objects, effects, features and advantages of the present invention will become more apparent from the following description of embodiments thereof taken in conjunction with the accompanying drawings.

BRIEF DESCRIPTION OF THE DRAWINGS

FIGS. 1 to 3 are schematic cross-sectional views of photoconductors according to the present invention.

DETAILED DESCRIPTION OF PREFERRED EMBODIMENTS

The photoconductor according to the present invention which contains a novel compound as a charge transporting substance in the photosensitive layer thereof may be in the form of any one of the structures of FIGS. 1, 2 and 3, depending on the way of application of this compound.

FIGS. 1, 2 and 3 are schematic cross-sectional views of different embodiments of the photoconductor of the present invention, respectively.

FIG. 1 shown a monolayer type photoconductor. A photosensitive layer 2A is provided on an electroconductive substrate 1. The photosensitive layer 2A comprises a charge generating substance 3 and a novel compound as a charge transporting substance 5, which will be explained later, both of which substances are dispersed in a resin binder, as a result, the photosensitive layer 2A functions as photoconductor.

FIG. 2 shown a laminate type photoconductor. A laminated photoconductive Layer 2B is provided on an electroconductive substrate 1, an lower of the laminate is a charge generating layer 4 including a charge generating substance 3 as a main component and an upper one is a charge transporting layer 6 containing a specific compound as a charge transporting substance, as a result, the photosensitive layer 2B functions as a photoconductor. A covering layer 7 can be generally provided as shown in FIG. 3 if necessary.

FIG. 3 shown another laminate type photoconductor having a photosensitive layer 2C of the structure in reverse to that of FIG. 2. A laminated photosensitive layer 2C is provided on an electroconductive substrate 1, a lower layer of the laminate is a charge transporting layer 6 including a specific compound as a charge transporting substance and an upper one is a charge generating layer 4 including a charge generating substance 3. The photosensitive layer also functions as a photoconductor. This photoconductor us usually used according to the positive charge mode. In this case, a covering layer 7 may generally be further provided as shown in FIG. 3 to protect the charge generating layer 4.

Thus, there are two different types of layer structures in the photoconductor. The reason for this is that, even if any photoconductor with the layer structure as shown in FIG. 2 is to be used in the positive charge mode, no charge transporting substances adaptable to the positive charge mode have been found yet. Accordingly, when the positive charge mode is adapted, the photoconductor is required of a layer structure as shown in FIG. 3 at present.

A photoconductor as shown in FIG. 1 can be produced by dispersing a charge generating substance in a solution of a specific compound as a charge transporting substance and a resin binder and applying the resulting dispersion on an electroconductive substrate.

A photoconductor as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a specific compound as a charge transporting substance and a resin binder on the resulting layer and drying.

A photoconductor as shown in FIG. 3 can be prepared by applying and drying a solution of a specific compound as a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the coating layer, followed by formation of a covering layer.

The electroconductive substrate 1 serves as an electrode of the photoconductor and as a support for a layer or layers formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a particulate charge generating substance 3 in a resin binder or by deposition of a charge generating substance by means of vacuum evaporation, or the like technique as described above, and this layer generates an electric charge upon receiving light. It is important that the charge generating layer 4 be high no only in charge generating efficiency but also in capability of injecting the generated electric charge into the charge transporting layer 6 and any covering layer 7, whose capability is desirably as little dependent upon the electric field as possible and high even in low intensity electric fields.

Usable charge generating substances include metal-free phthalocyanine, phthalocyanine compounds such as titanyl phthalocyanine; various azo, quinone and indigo pigments; dyes such a cyanine, squarylium, azulenium, and pyrylium compounds; and selenium and selenium compounds. Among them, a suitable compound can be chosen depending on the wavelength range of a light source used for the image formation. The thickness of the charge generating layer is determined depending on the extinction coefficient of a charge generating substance to be used therein in view of the layer's function of generating an electric charge, but is generally 5 μm or smaller, preferably 1 μm or smaller. It also is possible to form a charge generating layer using a charge generating substance as a main component in mixture with a charge transporting substance and so on.

Resin binders include polycarbonates, polyester, polyamides, polyurethanes, vinyl chloride resins, epoxy resins, diallylphthalate resins, silicone resins, and methacrylate ester homopolymer and copolymers, which may be used either alone or in an appropriate composition ratio.

The charge transporting layer 6 is a coating film containing a compound represented by the above-mentioned general formula (I) of (II), which will be described later in detail, as an organic charge transporting substance in a resin binder. The charge transporting layer serves as an insulator layer in the dark so as to retain the electric charge of the photoconductor, and fulfills a function of transporting an electric charge injected from the charge generating layer upon receiving light. Resin binders include polycarbonates, polyesters, and methacrylate ester homopolymer and copolymers.

The ratio of the compounds represented by the above-mentioned general formula (I) or (II) to resin binders is from 30 wt% to 80 wt%, preferably from 40 wt% to 60 wt%. Chloroform, dichloromethane, benzene, toluene, methye ethyl ketone, tetrahydrofuran et al are used as a solvent.

The covering layer 7 has a function of receiving and retaining an electric charge generated by corona discharge in the dark and a capability of transmitting light to which the charge generating layer should respond. It is necessary that the covering layer transmits light upon exposure of the photoconductor and allows the light to reach the charge generating layer, and then undergoes the injection of an electric charge generated in the charge generating layer to neutralize and erases a surface electric charge.

Materials usable in the covering layer include organic insulating film-forming materials such as polyesters and polyamides. Such organic materials may also be used in mixture with an inorganic material such as a glass resin or $SiO_2$, or a material for lowering electric resistance such as a metal or a metallic oxide. Materials usable in the covering layer are not limited to organic insulating materials for film-forming, and further include inorganic materials such as $SiO_2$, metals, and metallic oxides, which may be formed into a covering layer by an appropriate method such as vacuum evaporation, deposition, or sputtering.

From the viewpoint of the aforementioned description, it is desirable that the material to be used in the covering layer be as transparent as possible in the wavelength range in which the charge generating substance attains maximum light absorption.

Although the thickness of the covering layer depends on the material or composition thereof, it can be arbitrarily set so far as it does not produce any adverse effects including an increase in a residual potential in continuous repeated use.

The first group of the compound used as a charge transporting substance is represented by the following general formula (I):

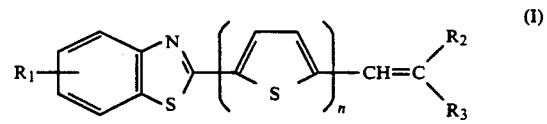

(I)

The compounds represented by the above-mentioned formula (I) used in the present invention can be easily synthesized by the Wittig reaction, that is, by reacting the aldehydes represented by the following general formula (1) with the Wittig reagent (2) or (3):

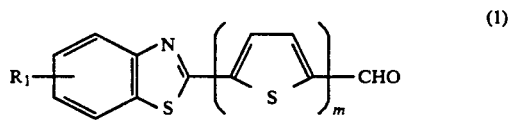

(1)

Wherein, R1 is selected from the group consisting of a hydrogen atom, a halogen atom, an alkyl group and an alkoxy group, and n is an integer of 1 or 2.

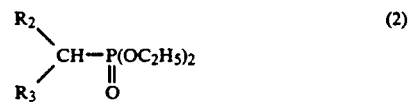

(2)

Wherein each of R2 and R3 is selected from the group consisting of an alkyl group, an aryl group and a heterocyclic group, the last two groups of which may be substituted.

(3)

Wherein, each of R5 and R6 is selected from the group consisting of an alkyl group, an aryl group and a heterocyclic group, the last two groups of which may be substituted.
Specific examples of the compounds represented by the general formula (I) thus obtained include:
compound No I-1
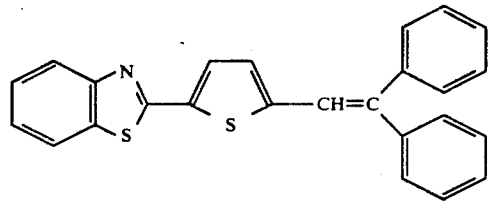
No I-2
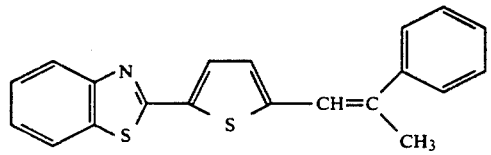
No I-3
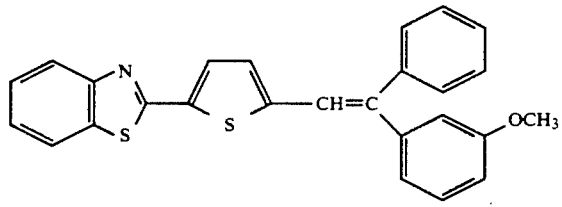
No I-4
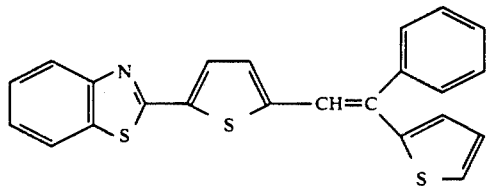
No I-5
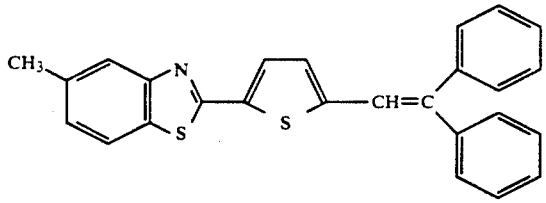
No I-6
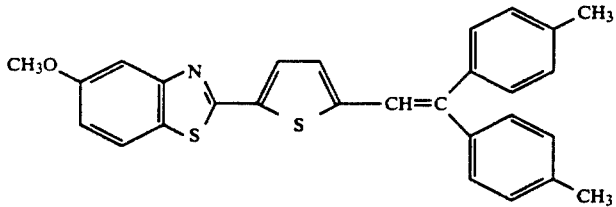
No I-7
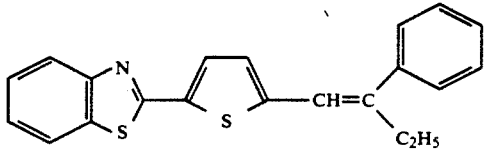

-continued

No I-8
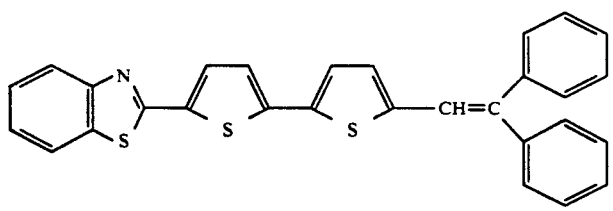

No I-9
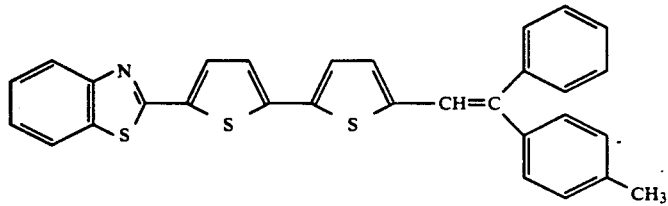

No I-10
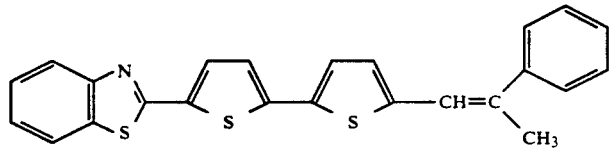

No I-11
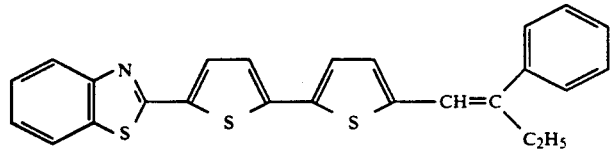

No I-12
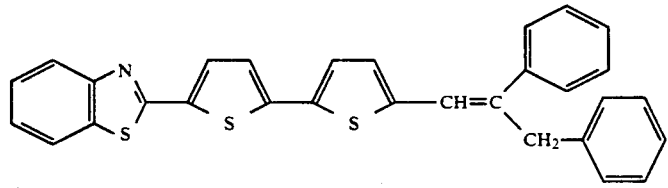

No I-13
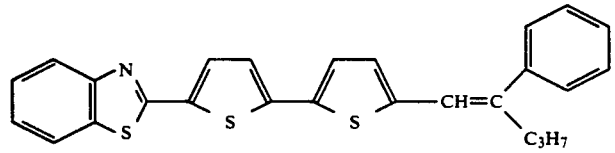

The second group of the compounds used as a charge transporting substance is represented by the following general formula (II):

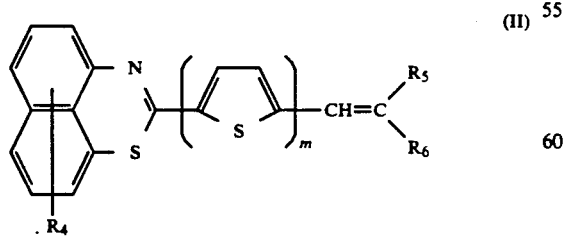
(II)

The compounds represented by the above-mentioned formula (II) used in the present invention can be easily synthesized by the Wittig reaction, that is, by reacting the aldehydes represented by the following general formula (4) with the Wittig reagent (2) or (3):

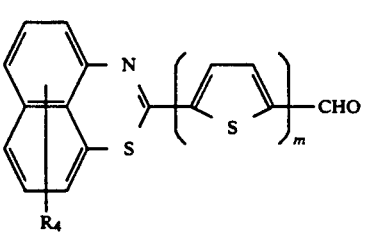
(4)

Wherein, $R_4$ is selected from the group consisting of a hydrogen atom, a halogen atom, an alkyl group and an alkoxy group, and m is an integer of 1 or 2.

Specific examples of the compounds represented by the general formula (II) thus obtained include:

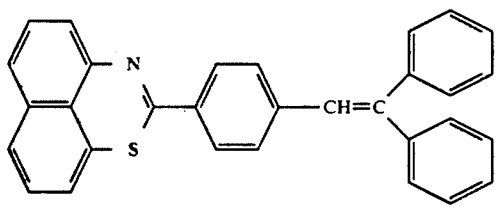
compound No II-1
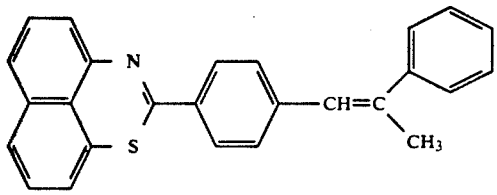
No II-2
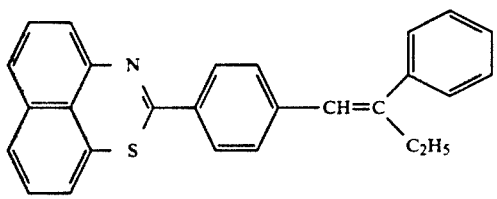
No II-3
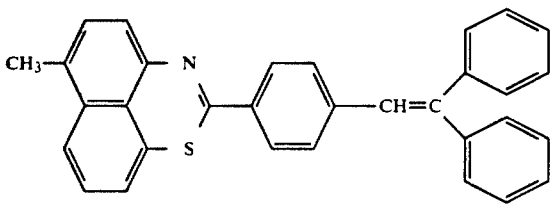
No II-4
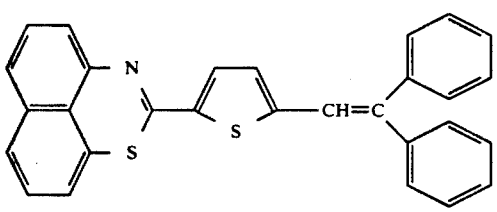
No II-5
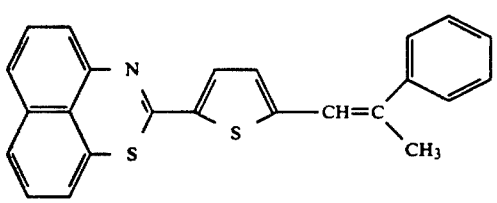
No II-6
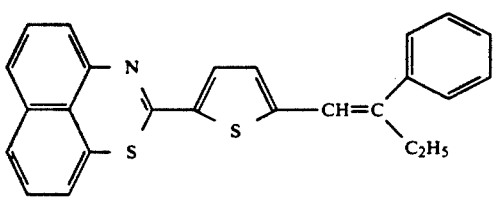
No II-7

-continued

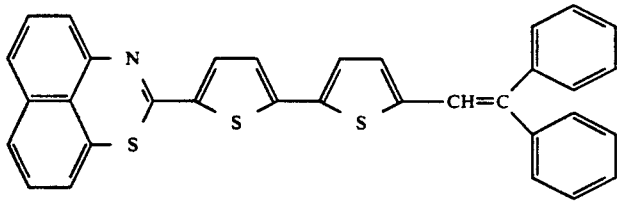
No II-8

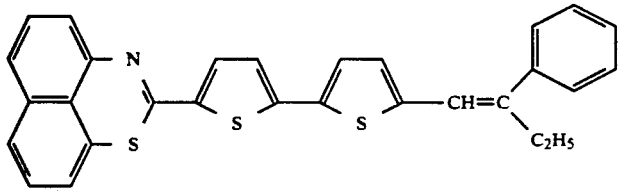
No II-9

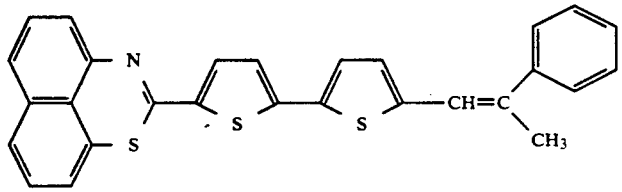
No II-10

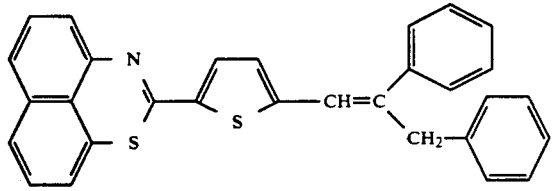
No II-11

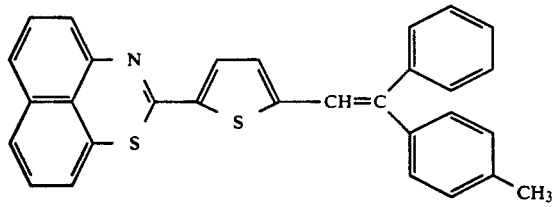
No II-12

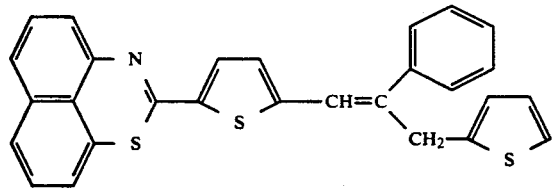
No II-13

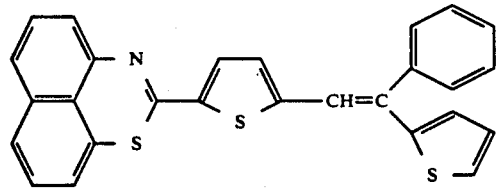
No II-14

Examples will now be given, wherein various compounds represented by the general formula (I) or (II) were respectively used to produce photoconductors.

EXAMPLE 1

50 parts by weight of metal-free phthalocyanine (H2 Pc) of an X type and 100 parts by weight of the above-mentioned compounds No. I-1 were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied onto an aluminum-deposited polyester film (Al-PET) as an electroconductive substrate by means of the wire bar method to form a photosensitive layer having a dry thickness of 15 μm.

EXAMPLE 2

80 parts by weight of the above-mentioned compound No. I-2 and 100 parts by weight of a polycarbonate resin (Panlite (Trademark) L-1225, manufactured by Teijin Kasei Co., Ltd.) are dissolved in methylene chloride to prepare a coating liquid. The coating liquid was applied onto the aluminum-deposited polyester film substrate by means of the wire bar method to form a charge transporting layer having a dry thickness of 15 μm. 50 parts by weight of titanyl phthalocyanine (TiOPc) pulverized with a ball mill for 150 hours and 50 parts by weight of a polyester resin (Vylon 200) were kneaded together with THF as a solvent by a mixer for 3 hours to prepare a coating liquid. The coating liquid was applied onto the charge transporting layer obtained as mentioned above by the wire bar method to form a charge generating layer having a dry thickness of 1 μm and then form a covering layer. In this way, the photoconductor was produced.

EXAMPLE 3

A photoconductor was produced in substantially the same manner as in Example 2 except that a squarylium compound represented by the following formula instead of TiOPc and the above-mentioned compound No. I-3 as a charge transporting substance were used.

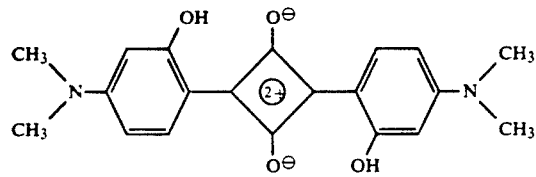

EXAMPLE 4

A photoconductor was produced by forming a photosensitive layer in substantially the same manner as in Example 2 except that Chlorodiane blue which is a bisazo pigment disclosed in, for example, Japanese Patent Application Laying-open No. 37,543/1972 instead of TiOPc and the above-mentioned compound No. I-4 as a charge transporting substance were used.

The electrophotographic characteristics of the four photoconductors thus produced were measured by utilizing an electrostatic recording paper testing apparatus (Kawaguchi Denki Model SP-428).

The surface potential Vs (volts) of each photoconductor is an initial surface potential which was measured when the surface of the photoconductor was positively charged in the dark by corona discharge at +6.0 kV for 10 seconds. After the discontinuation of the corona discharge, each photoconductor was allowed to stand in the dark for 2 seconds, after which the surface potential Vd (volts) of each photoconductor was measured. Subsequently, the surface of each photoconductor was irradiated with white light at an illuminance of 2 luxes and the time (seconds) required for the irradiation to decrease the surface potential of each photoconductor to a half of Vd was measured, then from which the half decay exposure amount $E_{\frac{1}{2}}$ (lux second) was calculated. Also, the surface potential of each photoconductor after 10 seconds of irradiation thereof with white light at an illuminance of 2 luxes was measured as a residial potential Vr (volts). As to the photoconductors of Example 1-3, a high sensitivity could be expected for light with longer wavelengths. Hence, the electrophotographic characteristics thereof were also measured by using a monochromatic light with a wavelength of 780 nm. Specifically, the Vs and the Vd of each photoconductor were measured in the same manner as described above, and the half decay exposure amount ($\mu J/cm^2$) was found by irradiation of the photoconductor surface with a monochromatic light (wavelength: 780 nm) of 1 μW instead of white light, while the residual potential Vr (volts) was measured after 10 second of irradiation of the photoconductor surface with the above-mentioned light. The results of the measurements are shown in Table 1.

TABLE 1

| | White Light | | | Light with a wavelength of 780 nm | | |
|---|---|---|---|---|---|---|
| Example | Vs (volts) | Vr (volts) | $E_{\frac{1}{2}}$ (lux · second) | Vs (volts) | Vr (volts) | $E_{\frac{1}{2}}$ (lux · second) |
| 1 | 720 | 60 | 3.5 | 750 | 60 | 2.8 |
| 2 | 750 | 20 | 2.0 | 710 | 30 | 1.5 |
| 3 | 760 | 30 | 2.1 | 770 | 20 | 1.3 |
| 4 | 770 | 20 | 1.2 | — | — | — |

As can be seen in Table 1, the photoconductors of Examples 1 to 3 were not substantially different therebetween in the half decay exposure amounts and the residual potentials, and showed good surface potential characteristics. The photoconductors of Examples 1 to 3 showed also excellent electrophotographic characteristics for light with a long wavelength of 780 nm. These photoconductors of Examples 1 to 3 can be used for a semiconductor laser printer.

In addition, when the surface potentials of Examples 1 to 3 were repeatedly measured 100 times, the variations of the surface potentials before exposure were within 70 V and the variations of the surface potentials after exposure were within 10 V. The stabilities in repeated uses also showed excellent results.

EXAMPLE 5

Selenium was deposited on an aluminum plate having a thickness of 500 μm by means of vacuum evaporation to form a charge generating layer having a thickness of 1.5 μm. 100 parts by weight of the compound No. II-1 and 100 parts by weight of polycarbonate resin (PCZ 200 (trademark), manufactured by Mitsubishi Gas Kagaku Co., Ltd.) were solved in methylene chloride to form a coating liquid. The coating liquid was applied by means of the wire bar method to the charge generating layer to form a charge transporting layer having a dry thickness of 20 μm. Thus, a photoconductor was produced. This photoconductor was charged in the dark by corona discharge at −6 KV for 10 seconds. Then, the electrophotographic characteristics of the photoconductor was measured with white light. As a result, good results were obtained, namely, Vs=−700 V, Vr=−20 V and $E_{\frac{1}{2}}$=1.5 lux.second.

EXAMPLE 6

As the same method as Example 2, 50 parts by weight of metal-free phthalocyanine of an X type pulverized with a ball mill for 150 hours and 50 parts by weight of vinyl chloride copolymer (MR-110 (trademark), manufactured by Nihon Zeon Co., Ltd.) were kneaded together with methylene chloride by use of a mixer for 3 hours to prepare a coating liquid. The coating liquid was applied on to an aluminum substrate to a form a charge generating layer having a thickness of about 1 μm. Subsequently, 100 parts by weight of the foregoing compound No. II-2, 100 parts by weight of polycarbonate resin (Panlite L-1250 (trademark)) and 0.1 part by weight of silicone oil were mixed with methylene chloride to prepare a coating liquid. The coating liquid was applied to the charge generating layer having a thickness of about 15 μm to form a charge transporting layer, thus a photoconductor was obtained.

The electrophotographic characteristics of the photoconductor thus obtained were measured in the same manner as in Example 5. The Example 6 showed good results, namely, Vs= −720 V and E½ = 1.3 lux.second.

EXAMPLE 7

A photoconductor was produced in the same manner as in Example 6 except that a bisazo pigment of the following general formula was used instead of metal-free phthalocyanine and the above-mentioned compound No. II-3 was used as a charge transporting substance:

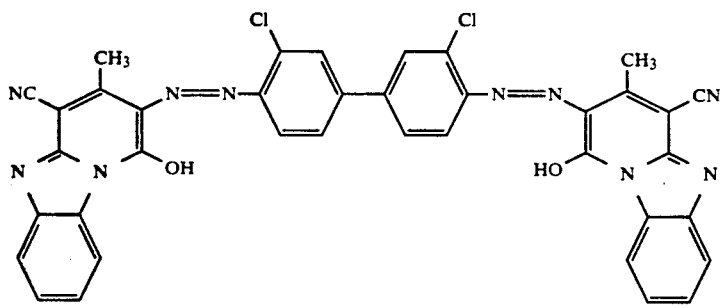

The electrophotographic characteristics of the photoconductor thus obtained was measured in the same manner as in Example 5.

The Example 7 shown good results, namely, Vs= −690 V and E½ = 1.4 lux.second.

EXAMPLE 8

Photoconductors were respectively produced in the same manner as in Example 4 except that the compounds No. I-5 to No. I-13 and No. II-4 to No. II-14 are respectively used as a charge transporting substance. The electrophotographic characteristics of the photoconductors were measured by use of the electrostatic recording paper testing apparatus Model SP-428.

The half decay exposure amounts E½ (lux.second), when the photoconductors were positively charged by corona discharge in the dark at +6.0 kV for 10 seconds and irradiated with white light at an illuminance of 2 luxes, were measured. The results thus obtained were shown in Table 2.

TABLE 2

| Compound No. | E½ (lux · second) | Compound No. | E½ (lux · second) |
|---|---|---|---|
| I-5 | 1.2 | II-5 | 2.1 |
| I-6 | 1.5 | II-6 | 1.8 |
| I-6 | 1.8 | II-6 | 1.6 |
| I-7 | 1.6 | II-7 | 1.9 |
| I-8 | 2.2 | II-8 | 1.5 |
| I-9 | 1.6 | II-9 | 1.9 |
| I-10 | 1.5 | II-10 | 2.1 |
| I-11 | 1.7 | II-11 | 2.9 |
| I-12 | 2.2 | II-12 | 2.3 |
| I-13 | 1.8 | II-13 | 1.7 |
| II-4 | 1.5 | II-14 | 2.0 |

As can be seen in Table 2, the photoconductors using the respective compounds No. I-5 to No. I-13 and No. II-4 to No. II-14 as a charge transporting substance were satisfactory with respect to the half decay exposure amounts E½.

According to the present invention, since a compound represented by any one of the aforementioned general formula (I) or (II) is used as a charge transporting substance, a photoconductor having a photosensitive layer in the structure of a monolayer type or a laminate type shows also a high sensitivity and excellent characteristics in repeated use when adapted to either a positive charge mode or a negative charge mode.

A suitable charge generating substance can be chosen so as to be adapted the kind of exposure light source. By way of example, a phthalocyanine compound, a squarylium compound and a bisazo compound can be used as a charge generating substance to provide a photoconductor capable of being used in semiconductor laser printers. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A photoconductor for electrophotography comprising:
   an electroconductive substrate; and
   a photosensitive layer formed on said electroconductive substrate including a charge generating substance and at least one of the compounds represented by the following general formula (I) as a charge transporting substance:

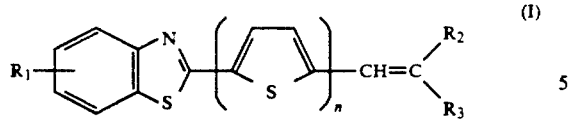

wherein, R1 is selected from the group consisting of a hydrogen atom, a halogen atom, an alkyl group and an alkoxy group, each of R2 and R3 is selected from the group consisting of an alkyl group, an aryl group and a heterocyclic group, the last two groups of which may be substituted, and n is an integer of 1 or 2.

2. A photoconductor as claimed in claim 1, wherein said photosensitive layer is a monolayer containing a charge generating substance and a charge transporting substance.

3. A photoconductor as claimed in claim 1, wherein said photosensitive layer is composed of a charge generating layer containing a charge generating substance and a charge transporting layer containing said charge transporting substance and laminated on the charge generating layer.

4. A photoconductor as claimed in claim 1, wherein said photosensitive layer is composed of a charge transporting layer containing said charge transporting substance and a charge generating layer containing a charge generating substance and laminated on the charge transporting layer.

5. A photoconductor for electrophotography comprising:
an electroconductive substance; and
a photosensitive layer formed on said electroconductive substrate including a charge generating substance and at least one of the compounds represented by the following general formula (II) as a charge transporting substance:

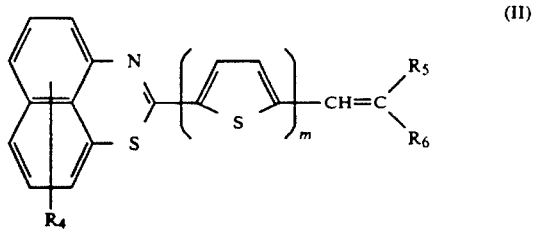

wherein, R4 is selected from the group consisting of a hydrogen atom, a halogen atom, an alkyl group and an alkoxy group, each of R5 and R6 is selected from the group consisting of an alkyl group, an aryl group and a heterocyclic group, the last two groups of which may be substituted, and m is an integer of 1 or 2.

6. A photoconductor as claimed in claim 5, wherein said photosensitive layer is a monolayer containing a charge generating substance and said charge transporting substance.

7. A photoconductor as claimed in claim 5, wherein said photosensitive layer is composed of a charge generating layer containing a charge generating substance and a charge transporting layer containing said charge transporting substance and laminated on the charge generating layer.

8. A photoconductor as claimed in claim 5, wherein said photosensitive layer is composed of a charge transporting layer containing said charge transporting substance and a charge generating layer containing a charge generating substance and laminated on the charge transporting layer.

* * * * *